United States Patent
Ross et al.

(10) Patent No.: US 8,131,483 B2
(45) Date of Patent: Mar. 6, 2012

(54) YARN ENTANGLEMENT STRENGTH TESTER

(75) Inventors: Dean A. Ross, Riverside, RI (US); Filiz Avsar, Fall River, MA (US); Kendall W. Gordon, Exeter, RI (US); Steven Leary, Berkley, MA (US)

(73) Assignee: Testing Machines, Inc., New Castle, DE (US)

( * ) Notice: Subject to any disclaimer, the term of this patent is extended or adjusted under 35 U.S.C. 154(b) by 25 days.

(21) Appl. No.: 12/775,827

(22) Filed: May 7, 2010

(65) Prior Publication Data

US 2011/0276280 A1 Nov. 10, 2011

(51) Int. Cl.
*G01L 1/24* (2006.01)
*G01N 21/00* (2006.01)
*B65H 23/08* (2006.01)
(52) U.S. Cl. .......... 702/41; 702/42; 226/195; 356/238.2
(58) Field of Classification Search ................ 356/238.2
See application file for complete search history.

(56) References Cited

U.S. PATENT DOCUMENTS

| | | | | |
|---|---|---|---|---|
| 4,719,576 A * | 1/1988 | Sano et al. | ..................... | 700/144 |
| 5,319,578 A * | 6/1994 | Lawson et al. | ............ | 250/559.24 |
| 5,791,542 A * | 8/1998 | Porat et al. | ....................... | 226/44 |
| 6,130,746 A | 10/2000 | Nevel et al. | ................. | 356/238.2 |
| 6,741,726 B1 | 5/2004 | Nevel et al. | .................... | 382/111 |
| 2002/0189703 A1* | 12/2002 | Medeiros et al. | ......... | 139/420 R |
| 2004/0074942 A1* | 4/2004 | Sorebo et al. | ............... | 226/118.2 |
| 2004/0118892 A1* | 6/2004 | Weber et al. | .................... | 226/44 |
| 2010/0233480 A1* | 9/2010 | Hu et al. | ....................... | 428/401 |

* cited by examiner

*Primary Examiner* — Jonathan C Teixeira Moffat
(74) *Attorney, Agent, or Firm* — Harrity & Harrity, LLP

(57) ABSTRACT

A yarn entanglement strength tester includes first and second rolls that apply incrementally increasing elongation levels on a yarn in order to remove entanglements from the yarn. The yarn entanglement strength tester also includes a third roll, where the second and third rolls apply a constant tension on the yarn which enables optimum diameter measurements of the yarn by a camera. The camera captures images of diameters of the yarn after each of the incrementally increasing elongation levels is applied to the yarn. The yarn entanglement strength tester further includes a computing device that controls operation of the camera and the first, second, and third rolls, and determines an entanglement strength of the yarn based on the captured images of the diameters of the yarn after each of the incrementally increasing elongation levels is applied to the yarn.

24 Claims, 9 Drawing Sheets

FIG. 6

TEST DATA

| Test # | E% | Tension | ES% | E-Count | Ave Skip (cm) | Max Skip (cm) | SD (cm) | CV% |
|---|---|---|---|---|---|---|---|---|
| 8 | 7.0 | 19.85 | 3.2 | 2.9 | 7.73 | 34.97 | 8.92 | 115.41 |
| 7 | 6.0 | 174.05 | 4.0 | 3.6 | 15.66 | 97.47 | 28.19 | 179.98 |
| 6 | 5.0 | 156.55 | 7.9 | 7.2 | 6.21 | 72.83 | 12.41 | 199.72 |
| 5 | 4.0 | 130.34 | 9.3 | 8.4 | 6.02 | 74.27 | 12.78 | 212.16 |
| 4 | 3.0 | 111.35 | 16.3 | 14.8 | 3.91 | 42.77 | 7.70 | 196.97 |
| 3 | 2.0 | 76.70 | 53.9 | 48.9 | 1.91 | 23.80 | 2.52 | 131.73 |
| 2 | 1.0 | 39.46 | 90.2 | 81.8 | 1.20 | 7.75 | 0.60 | 49.63 |
| 1 | 0.0 | 5.83 | 100.0 | 90.7 | 1.10 | 5.91 | 0.41 | 36.97 |

SUMMARY DATA

| ID | Pkg ID | E% | ES% | Tension | E-Count (ave) | Ave Skip (cm) | Max Skip (cm) | SD (cm) | CV% |
|---|---|---|---|---|---|---|---|---|---|
| 5 | 0.0 | 0.0 / 7.0 | 100.0 / 3.2 | 5.8 / 19.9 | 90.7 / 2.9 | 1.1 / 7.7 | 5.9 / 35.0 | 0.4 / 8.9 | 37.0 / 115.4 |
| 4 | 0.0 | 0.0 / 7.0 | 100.0 / 1.6 | 6.5 / 228.5 | 94.9 / 1.5 | 1.0 / 5.1 | 4.1 / 25.6 | 0.4 / 7.7 | 34.3 / 149.2 |
| 3 | 0.0 | 0.0 / 7.0 | 100.0 / 0.8 | 5.9 / 222.9 | 87.7 / 0.7 | 1.1 / 4.4 | 4.2 / 10.3 | 0.4 / 4.2 | 38.6 / 97.1 |

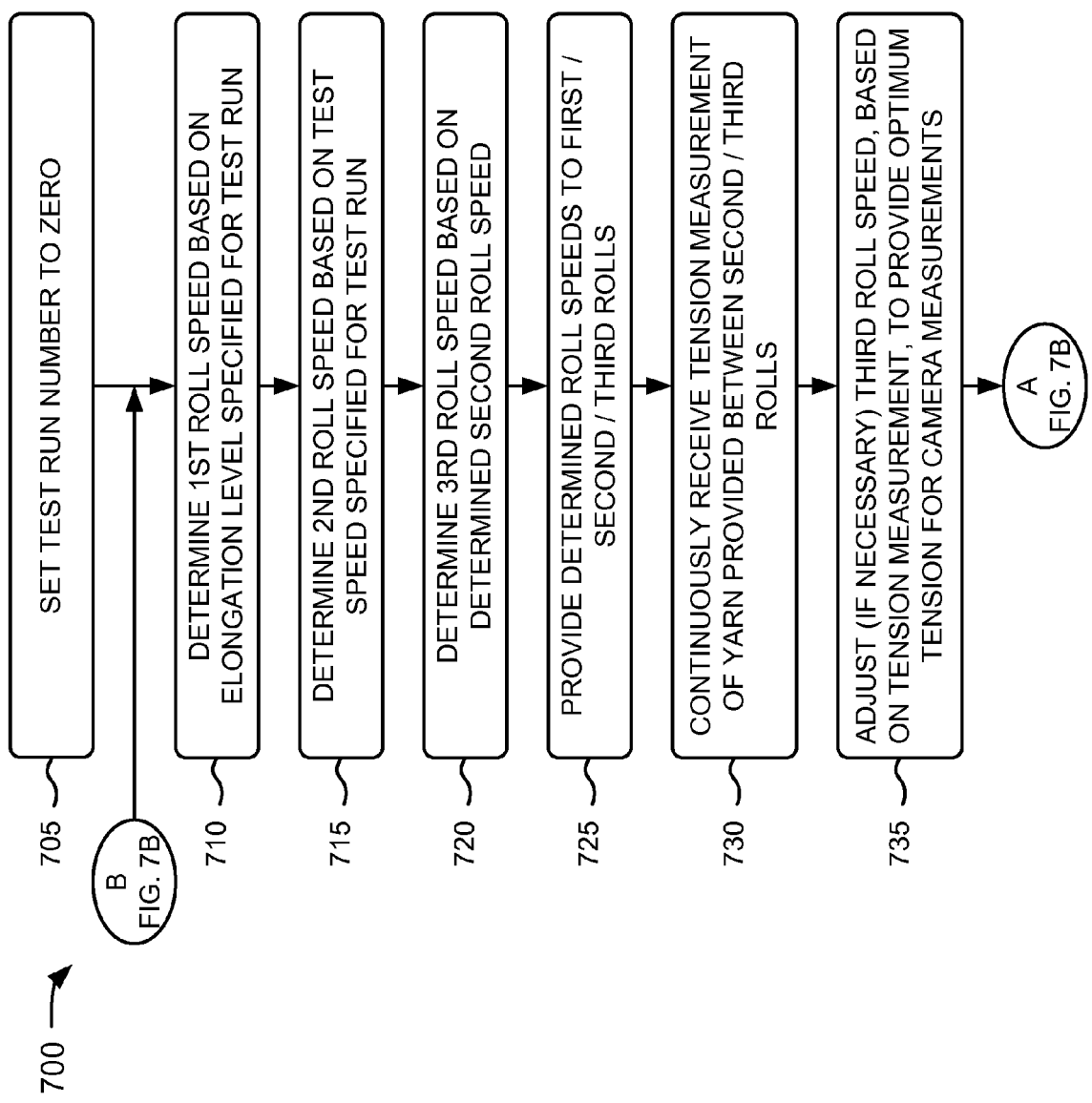

YARN ENTANGLEMENT STRENGTH TESTER

BACKGROUND

Fabric manufacturers want to know as much as possible about entangled yarn before it is used to manufacture fabric or other products. If the yarn does not have desired properties, there can be problems with a fabric production process as well as in a finished product made from the yarn. Some fabric manufacturers may specify yarn properties (e.g., to yarn producers), and the yarn producers may strive to provide yarn with such properties. In order to ensure that yarn has specified properties, the yarn producer may analyze and test the yarn for the properties.

Properties of entangled yarn include entanglement count and entanglement integrity or strength. Quality grade entangled yarn includes one or more entanglements and one or more skips. An "entanglement" refers to a section of yarn in which filaments are tightly intermingled as a result of passing through an entanglement jet of a texturizing machine. A "skip" refers to a section of yarn which is not intermingled and which is found prior to and after each entanglement. A good quality yarn, therefore, should have an equal, consistent, and predictable number of entanglements. The entanglement strength is another property of entangled yarn and is a measure of how strongly the entanglements are held in the yarn. As an indication of strength, entangled yarns are sometimes defined as "soft-entangled" and "hard-entangled," with the soft-entangled referring to entanglements that are easily removed from the yarn when the yarn is under tension and the hard-entangled referring to entanglements that are very resistant to removal.

Entanglement jets come in a variety of sizes, shapes, and designs that attempt to produce entanglements in yarn. The entanglements result from the air blast in the center of the jets (e.g., which causes the yarn filaments to spread) and from the yarn filaments on either side of the air blast winding themselves together. The end result after passing through an entanglement jet should be an even distribution profile of entanglements along the yarn. However, when entanglements are unevenly distributed, there are large skips between the entanglements.

If a distribution profile of yarn entanglements is inconsistent, properties of a fabric manufactured with the yarn may be inconsistent. For example, such fabric may have inconsistent reflectivity, which may cause different portions of the fabric to have different colors when dyed. Therefore, it is desirable to quantify and measure yarn entanglement properties in the lab in order to control such properties. For example, if a yarn is determined (e.g., via testing) to have an inconsistent distribution profile of yarn entanglements, the yarn manufacturer may alter process parameters (e.g., via changes to the entanglement jets being used) to improve the distribution profile of yarn entanglements.

The entanglements act to prevent individual filaments from flaring-out, spreading, or separating during processing of the yarn into a fabric, thereby maintaining a cohesive yarn bundle of filaments. The strength of an entanglement is related to its resistance to open or to remove the entangled sections of the yarn when under tension. Entanglement strength is a key element in beaming, knitting, and weaving performance of an entangled yarn. During the beaming process, tension is applied to the yarn which tends to cause the entanglements to pull out or became unraveled. Moreover, as beam yarn is supplied from the beam to a weaving or knitting machine the yarn again is subjected to tension. The fabric production performance is most affected by the knitting machine or weaving loom having to stop frequently because the individual yarn filament strands experience breaks or separation of the filaments due to a loss of entanglements in the yarn. Proper entanglement strength may result in a yarn that will be able to achieve highly efficient beaming, knitting, and weaving performance.

The distribution profile of yarn entanglements is currently tested via manual strength testing of the yarn entanglements. The manual strength test includes manually counting the number of entanglements that are in the yarn as taken from a bobbin or cone. After counting, a draw tension or tensile force is manually applied to the yarn, in an attempt to elongate the yarn and open or remove the entanglements in the yarn. Then the yarn is relaxed and a second manual count is made to determine how many entanglements remain in the yarn at the particular draw tension/tensile force. Some entanglements will be removed by the tensile force and some will not be removed. If a greater tensile force is applied to the yarn, even more entanglements will be removed from the yarn. However, such manual methods are time consuming and may lead to inaccuracies (e.g., due to human error).

BRIEF DESCRIPTION OF THE DRAWINGS

FIG. 6 is a diagram of a portion of a database capable of being provided in and/or managed by the computing device of the arrangement depicted in FIG. 1.

DETAILED DESCRIPTION

The following detailed description refers to the accompanying drawings. The same reference numbers in different drawings may identify the same or similar elements. Also, the following detailed description does not limit the invention.

Systems and/or methods described herein may enable entanglement strengths of yarn to be automatically and continuously tested. Such systems and/or methods may enable expedient and accurate testing of yarn entanglement strengths by eliminating the inordinate time and inaccuracies associated with manual testing. If the yarn is determined (e.g., via the automatic testing) to have an inconsistent distribution profile of yarn entanglements and/or an undesirable level or length of skips, the yarn manufacturer may alter process parameters (e.g., via changes to the entanglement jets being used) to improve the distribution profile of yarn entanglements.

Example Yarn Entanglement Strength Tester Arrangement

Figure 1:
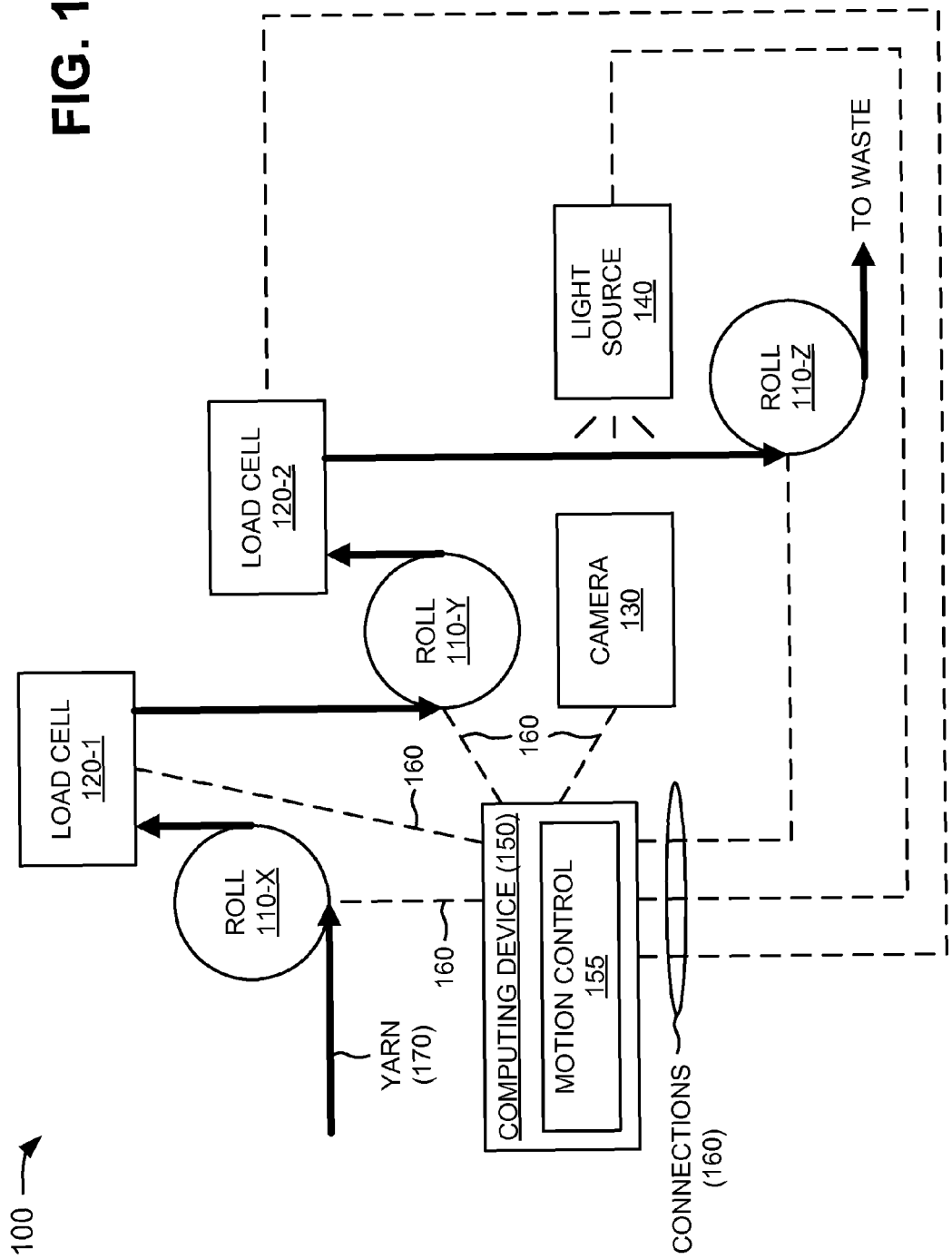
FIG. 1 is a diagram of an example arrangement in which systems and/or methods described herein may be implemented.

FIG. 1 is a diagram of an example arrangement 100 in which systems and/or methods described herein may be implemented. As illustrated, arrangement 100 may include rolls 110-X, 110-Y, and 110-Z (collectively referred to as "rolls 110," and, in some instances, individually as "roll 110"), load cells 120-1 and 120-2 (collectively referred to as "load cells 120," and, in some instances, individually as "load cell 120"), a camera 130, a light source 140, and a computing device 150. Computing device 150 may interconnect with rolls 110, load cells 120, camera 130, and light source 140 via wired and/or wireless connections 160 (e.g., Ethernet-based connections). Three rolls 110, two load cells 120, a single camera 130, a single light source 140, and a single computing device 150 have been illustrated in FIG. 1 for simplicity. In practice, there may be more rolls 110, load cells 120, cameras 130, light sources 140, and/or computing devices 150. Also, in some instances, one or more of the components of arrangement 100 may perform one or more functions described as being performed by another one or more of the components of arrangement 100.

Roll 110 may include a mechanism for moving yarn 170, provided from a cone of yarn (not shown), through arrangement 100. In one implementation, roll 110 may include a contact roller that engages yarn 170, rotates in a clockwise or counterclockwise direction (e.g., at a particular rotational speed), and causes yarn 170 to move through arrangement 100 (e.g., via the rotational movement). For example, roll 110-X may receive yarn 170 (e.g., from a cone of yarn), and may move yarn 170 through load cell 120-1 towards roll 110-Y. Roll 110-Y may receive yarn 170 from load cell 120-1, and may move yarn 170 through load cell 120-2 towards roll 110-Z (e.g., after passing through camera 130 and light source 140. Roll 110-Z may receive yarn 170 from load cell 120-2, and may move yarn 170 to waste.

In one particular implementation, roll 110-X and roll 110-Y may rotate at different rotational or roll speeds (e.g., roll 110-Y may rotate faster than roll 110-X) in order to apply a particular yarn draw ratio (e.g., a particular tensile force or elongation level) on yarn 170. In another implementation, roll 110-Y and roll 110-Z may rotate at different rotational or roll speeds (e.g., roll 110-Z may rotate faster than roll 110-Y) in order to apply a constant, reproducible tension on yarn 170 when yarn 170 passes between camera 130 and light source 140 (e.g., also referred to as an imaging area of arrangement 100). The constant, reproducible tension may enable the imaging area of arrangement 100 to determine useful, accurate, and quantitative data (e.g., an entanglement strength of yarn 170) concerning each cone of yarn that is measured by arrangement 100.

Load cell 120 may include a mechanism that measures a tensile force (e.g., a draw tension) on yarn 170. In one implementation, load cell 120 may include a transducer that converts the draw tension on yarn 170 into a measurable electrical output. In one example, load cell 120 may include strain gage-based load cell. With reference to FIG. 1, load cell 120-1 may measure a draw tension on the portion of yarn 170 provided between roll 110-X and roll 110-Y. Load cell 120-2 may measure a draw tension on the portion of yarn 170 provided between roll 110-Y and roll 110-Z.

Camera 130 may include a mechanism that captures images of yarn 170 (e.g., passing by camera 130), and provides the captured images to computing device 150. Camera 130 may include a device that may receive, capture, and store images and/or video. For example, camera 130 may include a digital camera, a video camera, etc. In one implementation, camera 130 may include a linear charged couple device (CCD) array. The amount of light sensed by each pixel of the CCD array may be provided as a related voltage or digital representation output of the CCD array.

Light source 140 may include a mechanism that illuminates yarn 170 passing between camera 130 and light source 140 (e.g., the imaging area). In one implementation, light source 140 may provide sufficient light in the imaging area of arrangement 100 so that an image of yarn 170 may be captured by camera 130. In one example, light source 140 may include a solid state light source or an incandescent lamp that may be regulated to provide a variable intensity, steady light source (e.g., without sixty Hertz flicker). The lamp may be associated with a fiber optic bundle that carries light from the lamp toward the measured yarn 170. Further details of camera 130 and light source 140 are provided below in connection with, for example, FIG. 4.

Computing device 150 may include a laptop computer, a personal computer, a tablet computer, or other types of computation or communication devices. In one example, computing device 150 may include a motion control module 155 that includes an Ethernet-based motion control device (e.g., for controlling motion associated with one or more components of arrangements 100).

In one implementation, computing device 150 (e.g., motion control module 155) may determine roll (or rotational) speeds for rolls 110-X, 110Y, and 110-Z based on a test being performed on yarn 170, and may provide the determined roll speeds to rolls 110-X, 110-Y, and 110-Z. Computing device 150 may receive (e.g., from load cell 120-1) a tension measurement associated with yarn 170 provided between rolls 110-X and 110-Y, and may adjust, if necessary, the roll speed(s) of rolls 110-X and/or 110-Y based on the tension measurement. Computing device 150 may receive (e.g., from load cell 120-2) another tension measurement associated with yarn 170 provided between rolls 110-Y and 110-Z, and may adjust, if necessary, the roll speed(s) of rolls 110-Y and/or 110-Z based on the other tension measurement. In another implementation, computing device 150 may set the roll speed(s) of rolls 110-X and/or 110-Y so that the roll speed(s) or rolls 110-Y and/or 110-Z are fixed according to test-specific speed parameters associated with the test being performed on yarn 170.

Computing device 150 may provide configuration information to camera 130 and light source 140 based on the test being performed on yarn 170, and may receive, from camera 130, diameter measurement information associated with yarn 170. Computing device 150 may analyze the diameter measurement information and may determine an entanglement count and entanglement strength of yarn 170 based on the diameter measurement information.

Although FIG. 1 shows example components of arrangement 100, in other implementations, arrangement 100 may contain fewer components, different components, differently arranged components, or additional components than depicted in FIG. 1.

Example Computing Device

Figure 2:
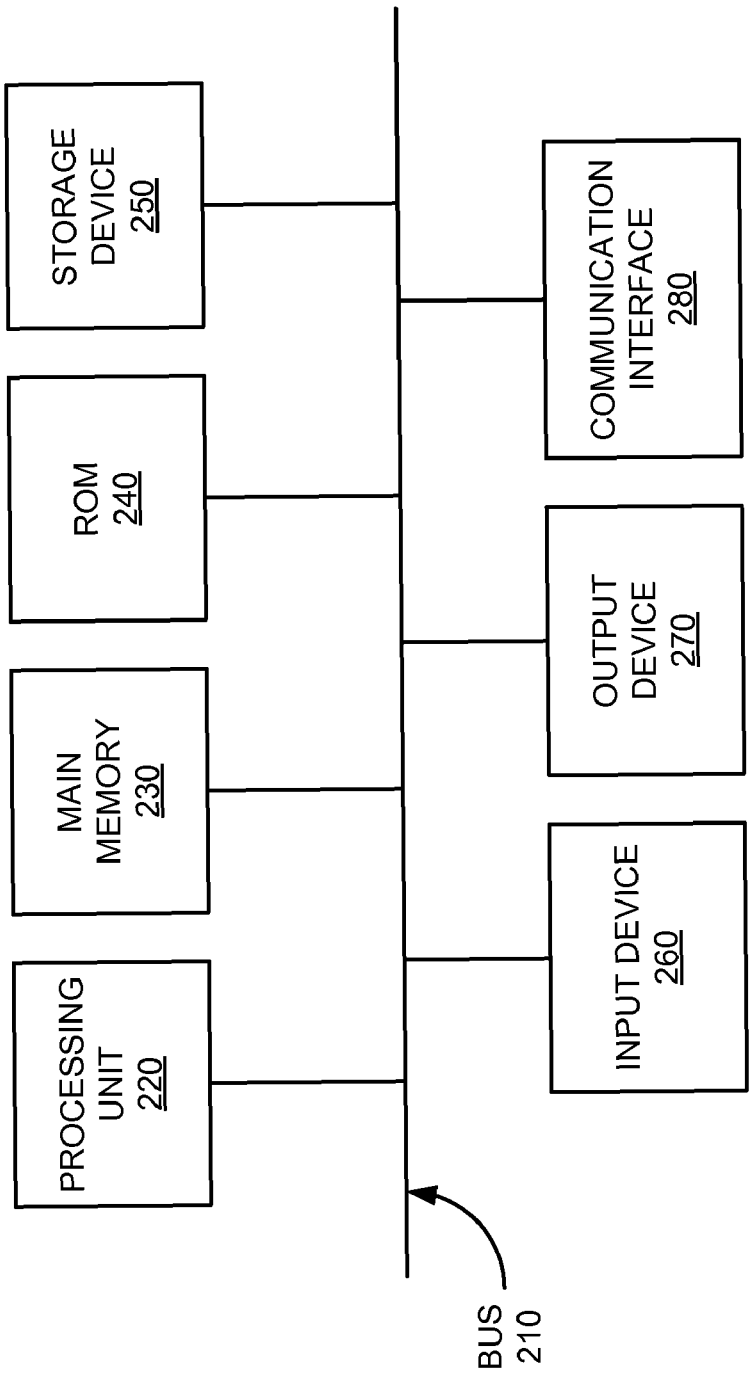
FIG. 2 is a diagram of example components of a computing device of the arrangement depicted in FIG. 1.

FIG. 2 is a diagram of example components of a device 200 that may correspond to computing device 150. As illustrated, device 200 may include a bus 210, a processing unit 220, a main memory 230, a read-only memory (ROM) 240, a storage device 250, an input device 260, an output device 270, and/or a communication interface 280. Bus 210 may include a path that permits communication among the components of device 200.

Processing unit 220 may include one or more processors, microprocessors, or other types of processing units that may interpret and execute instructions. Main memory 230 may include a random access memory (RAM) or another type of dynamic storage device that may store information and instructions for execution by processing unit 220. ROM 240 may include a ROM device or another type of static storage device that may store static information and/or instructions for use by processing unit 220. Storage device 250 may include a magnetic and/or optical recording medium and its corresponding drive.

Input device 260 may include a mechanism that permits an operator to input information to device 200, such as a keyboard, a mouse, a pen, a microphone, voice recognition and/or biometric mechanisms, a touch screen, etc. Output device 270 may include a mechanism that outputs information to the operator, including a display, a printer, a speaker, etc. Communication interface 280 may include any transceiver-like mechanism that enables device 200 to communicate with other devices and/or systems. For example, communication interface 280 may include mechanisms for communicating with another device or system via a network, such as an Ethernet-based network.

As described herein, device 200 may perform certain operations in response to processing unit 220 executing software instructions contained in a computer-readable medium, such as main memory 230. A computer-readable medium may be defined as a physical or logical memory device. A logical memory device may include memory space within a single physical memory device or spread across multiple physical memory devices. The software instructions may be read into main memory 230 from another computer-readable medium, such as storage device 250, or from another device via communication interface 280. The software instructions contained in main memory 230 may cause processing unit 220 to perform processes described herein. Alternatively, hardwired circuitry may be used in place of or in combination with software instructions to implement processes described herein. Thus, implementations described herein are not limited to any specific combination of hardware circuitry and software.

Although FIG. 2 shows example components of device 200, in other implementations, device 200 may contain fewer components, different components, differently arranged components, or additional components than depicted in FIG. 2. Alternatively or additionally, one or more components of device 200 may perform one or more other tasks described as being performed by one or more other components of device 200. For example, motion control module 155 (FIG. 1) may perform one or more operations described herein as being performed by computing device 150.

Example Distribution Profile of Yarn Entanglements

Figure 3:
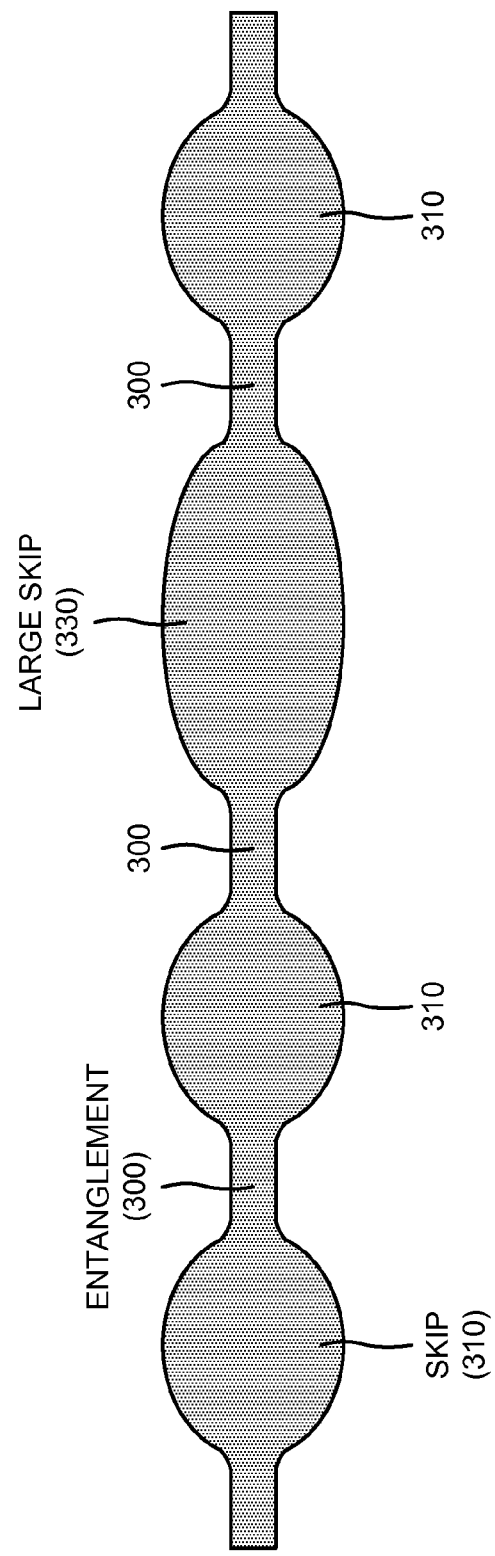
FIG. 3 is a diagram of an example distribution profile of yarn entanglements.

FIG. 3 is a diagram of an example distribution profile of entanglements provided in yarn 170. As shown, yarn 170 may include a number of entanglements 300 and a number of skips 310 provided between entanglements 300.

Each of entanglements 300 may include a section of yarn 170 in which filaments are tightly intermingled as a result of passing through an entanglement jet of a texturizing machine. Each of skips 310 may include a section of yarn 170 which is not intermingled and which is found prior to and after each entanglement 300.

A good quality yarn, therefore, should have an equal, consistent, and predictable number of entanglements 300. However, in one example and as further shown in FIG. 3, yarn 170 may include a large skip 330 in between two entanglements 300, which provides an inconsistent distribution profile of yarn entanglements. If a distribution profile of yarn entanglements is inconsistent, properties of a fabric manufactured with yarn 170 may be inconsistent. Arrangement 100 (FIG. 1) may enable detection of an inconsistent distribution profile of yarn entanglements via automatic and continuous testing of the entanglement strength of yarn 170.

Example Imaging Area of Yarn Entanglement Strength Tester

Figure 4:
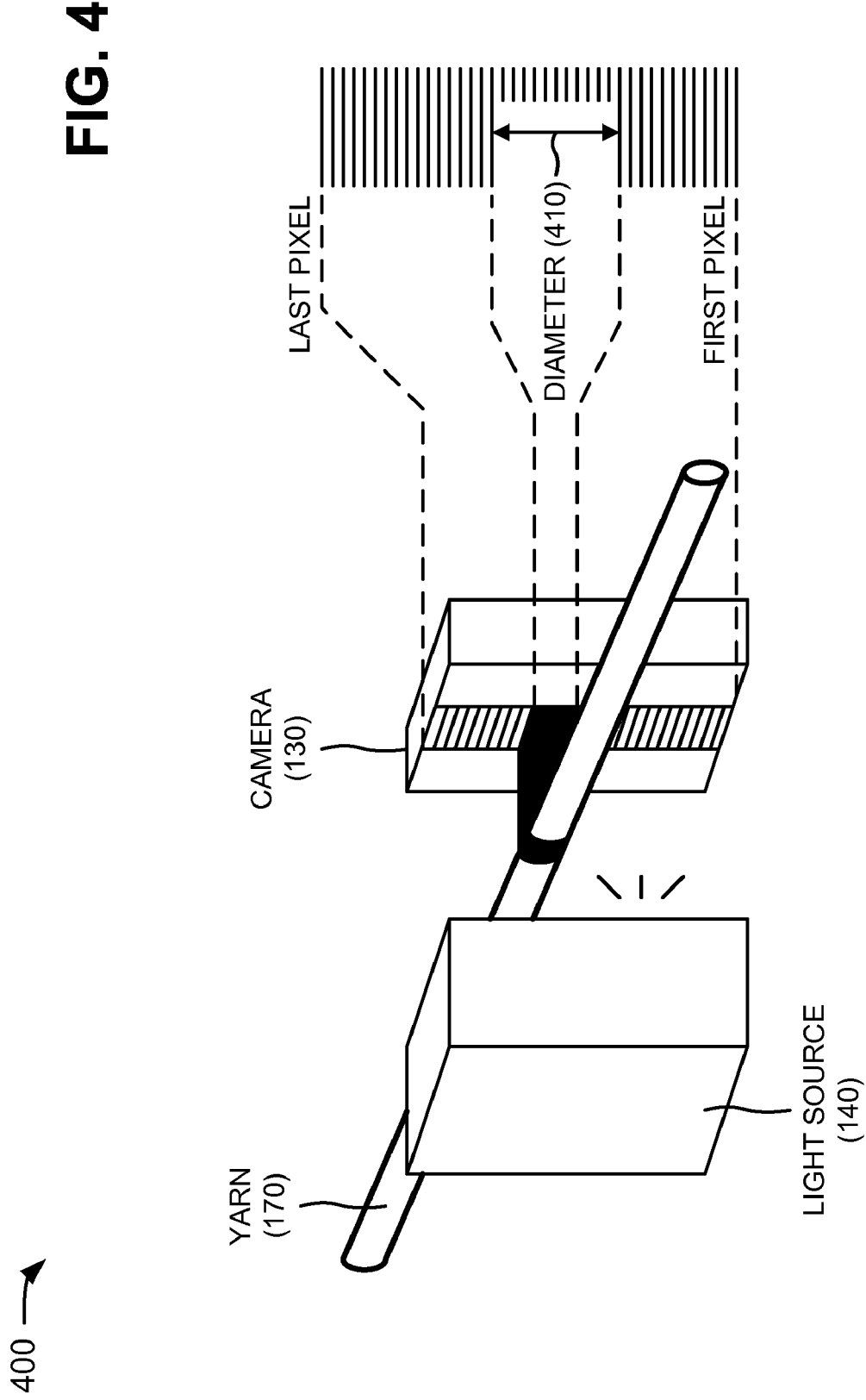
FIG. 4 is a diagram of particular operations capable of being performed by an imaging area of the arrangement depicted in FIG. 1.

FIG. 4 is a diagram of particular operations capable of being performed by an imaging area 400 of arrangement 100. As shown, imaging area 400 may include camera 130 and light source 140. Camera 130 and light source 140 may include the features described above in connection with FIG. 1.

Imaging area 400 may optically measure a diameter of yarn 170 while yarn 170 passes between camera 130 and light source 140. Camera 130 may include a CCD array of light receiving elements referred to as "pixels." When yarn 170 passes between camera 130 and light source 140, light (e.g., from light source 140) is projected on one side of yarn 170 and is either blocked by yarn 170 or received by a pixel of the CCD array of camera 130. The pixels that receive light may be considered "light" pixels, while pixels that do not receive light may be considered "dark" pixels. Camera 130 may provide such pixel information to computing device 150 (not shown), and computing device 150 may calculate a diameter 410 (e.g., in pixels) of yarn 170 as a distance between a first dark pixel and a last dark pixel, as shown in FIG. 4.

Computing device 150 may create a diameter graph by plotting the diameters of yarn 170 versus a length of yarn 170 moving past camera 130. Computing device 150 may create a yarn profile (e.g., of yarn 170) from the diameter graph. The yarn profile may include snapshot images of yarn 170 that are taken as yarn 170 passes by camera 130. Each snapshot image may be referred to as a "scan." In one implementation, a scan rate of camera 130 may be fixed, and, therefore, a number of scans per length of yarn 170 may depend on a test speed of yarn 170. In another implementation, the scan rate of camera 130 may be set by computing device 150 based on a test speed that provides a desired number of scans per length of yarn.

Although FIG. 4 shows example components of imaging area 400 of arrangement 100, in other implementations, imaging area 400 may contain fewer components, different components, differently arranged components, or additional components than depicted in FIG. 4. Alternatively or additionally, one or more components of imaging area 400 may perform one or more other tasks described as being performed by one or more other components of imaging area 400.

Example Operations of Yarn Entanglement Strength Tester

Figure 5:
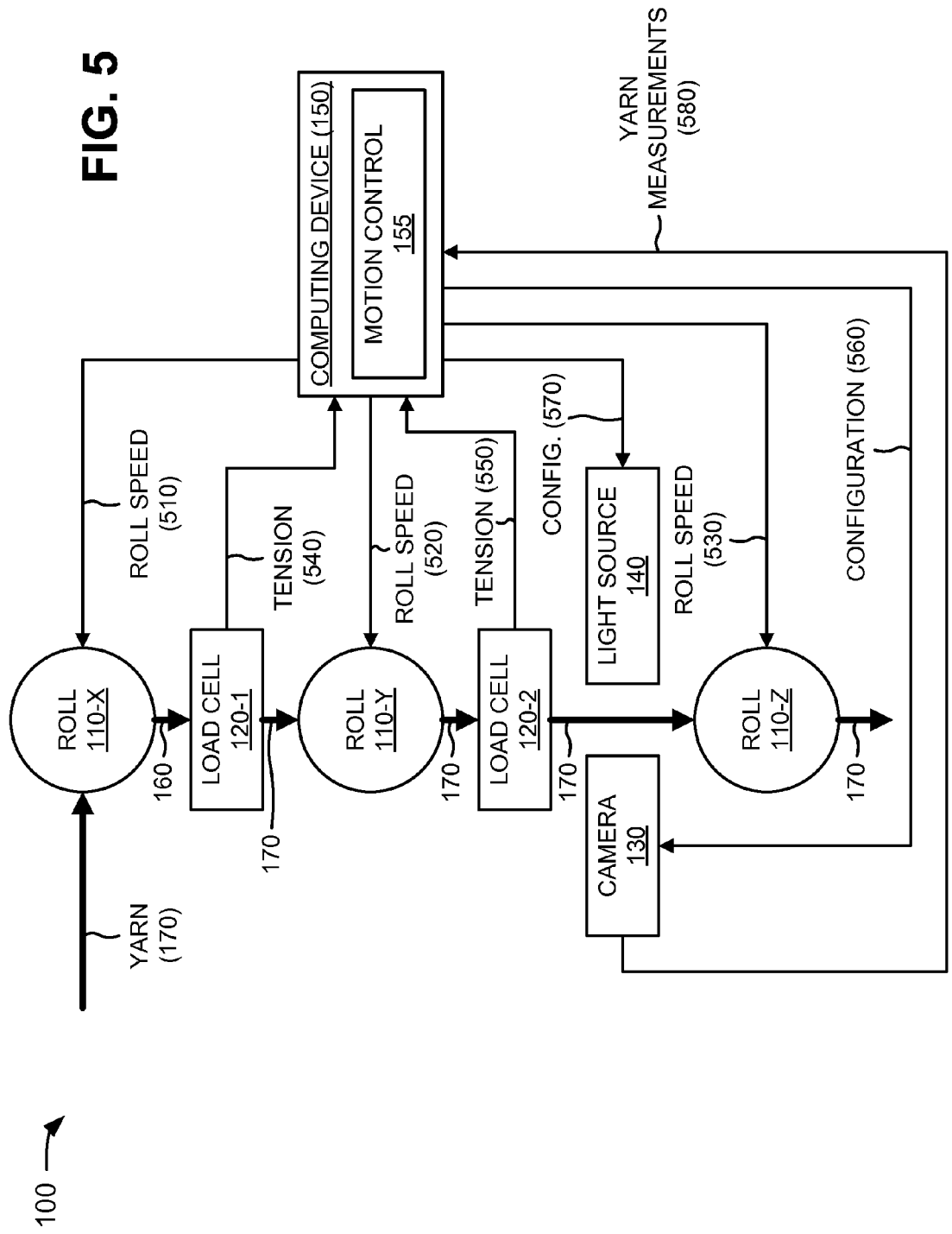
FIG. 5 is a diagram of particular operations capable of being performed by the arrangement depicted in FIG. 1.

FIG. 5 is a diagram of particular operations capable of being performed by arrangement 100. As shown, arrangement 100 may include rolls 110, load cells 120, camera 130, light source 140, and computing device 150. Rolls 110, load cells 120, camera 130, light source 140, and computing device 150 may include the features described above in connection with one or more of FIGS. 1, 2, and 4.

In one example, computing device 150 may implement an entanglement strength test of yarn 170 (e.g., via control of rolls 110, camera 130, and/or light source 140). The entanglement strength test may include executing a particular number (e.g., twenty) of test runs on a cone of yarn 170 (e.g., by continuously feeding new portions of yarn 170 towards camera 130 and light source 140). Each test run may include applying a different elongation level (e.g., a yarn draw ratio or draw tension) to yarn 170 in order to try to remove entanglements in yarn 170; stabilizing the tension on yarn 170 before it arrives at camera 130; measuring (e.g., via camera 130 and light source 140) a number of entanglements in the tension-stabilized yarn 170 at the applied elongation level; and comparing the measured number of entanglements in yarn 170 to an initial (e.g., at test run zero) number of entanglements in yarn 170 to determine an entanglement count and a number of entanglements remaining in yarn 170. Based on the number of entanglements remaining in yarn 170, computing device 150 may determine an entanglement strength percentage (or an entanglement retention value) associated with yarn 170, as described more fully below.

Computing device 150 may set a test run number to zero (e.g., an initial test number), and may determine roll speeds of rolls 110 based on a zero percent elongation level. In one example, the initial test run may not attempt to remove entanglements from yarn 170. Therefore, computing device 150 may determine a roll speed 510 for roll 110-X that is the same speed as a roll speed 520 determined for roll 110-Y (e.g., so that yarn 170 may be driven from roll 110-X towards roll 110-Y but no entanglements may be removed from yarn 170). As shown in FIG. 5, computing device 150 may provide roll speed 510 to roll 110-X and may provide roll speed 520 to roll 110-Y. Computing device 150 may determine a roll speed 530 for roll 110-Z that is greater than roll speed 520 determined for roll 110-Y. In one implementation, roll speeds 520/530 may be determined such that a tension value in yarn 170 (e.g., provided between rolls 110-Y and 110-Z) is a specific value (e.g., between ten to twenty grams) for providing optimum measurement of yarn 170 by camera 130. As shown in FIG. 5, computing device 150 may provide roll speed 530 to roll 110-Z. Rolls 110-X, 110-Y, and 110-Z may receive roll speeds 510-530, respectively, and may operate at roll speeds 510-530, respectively.

As further shown in FIG. 5, load cell 120-1 may measure a tension 540 of yarn 170 provided between rolls 110-X and 110-Y, and may provide tension 540 to computing device 150. In one example, computing device 150 may receive tension 540 and may record tension 540. In another example, computing device 150 may determine if tension 540 is appropriate for the initial test run (e.g., so that no entanglements are removed from yarn 170), and may adjust (if necessary) roll speeds 510 and/or 520 based on the determination. Load cell 120-2 may measure a tension 550 of yarn 170 provided between rolls 110-Y and 110-Z, and may provide tension 550 to computing device 150. Computing device 150 may receive tension 550, may determine if tension 550 is appropriate as an optimum tension for measurement by camera 130, and may adjust (if necessary) roll speeds 520 and/or 530 based on the determination. Computing device 150 may provide configuration information 560 to camera 130 and may provide configuration information 570 to light source 140. Configuration information 560 may include a scan rate of camera 130 and parameters such as exposure, pixel coefficients, camera gain, and other configuration parameters for camera 130. Configuration information 570 may include a light level to be provided by light source 140, a threshold for a desired light level to be provided by light source 140, etc.

As further shown in FIG. 5, camera 130 may provide yarn measurements 580 to computing device 150. Yarn measurements 580 may include diameters (e.g., a diameter profile) of yarn 170 that are captured by camera 130. Computing device 150 may also record a yarn elongation level (e.g., 0%) for the initial test run (e.g., based on roll speeds 510/520 and/or tension 540), may calculate an initial number of entanglements in yarn 170 (e.g., based on yarn measurements 580), and may calculate a percentage of entanglements remaining (e.g., 100%) in yarn 170 after the initial test run.

In one example, computing device 150 may set a threshold for determination of whether a diameter of yarn 170 constitutes an entanglement. If a diameter of yarn equals or is less than the entanglement threshold, computing device 150 may register the diameter as an entanglement (e.g., computing device 150 may increase an entanglement count by one). If a diameter of yarn 170 is greater than the entanglement threshold, computing device 150 may register the diameter as a skip. In one implementation, computing device 150 may measure the distance between threshold crossings to determine a length of a skip and/or a length of an entanglement. In another implementation, computing device 150 may filter out small unexpected crossings of the entanglement threshold that are too early for a valid new entanglement count.

After the initial test run, computing device 150 may increment the test run number by one (e.g., a first test run), and may set a specific elongation level for the test run (e.g., by fixing roll speeds of rolls 110 based on the test run number (e.g., one)). In one example, the first test run may attempt to remove some entanglements from yarn 170. Therefore, computing device 150 may determine roll speed 510 for roll 110-X that is less than roll speed 520 determined for roll 110-Y (e.g., so that a yarn draw tension is applied to yarn 170 that removes some entanglements from yarn 170). Computing device 150 may determine roll speed 530 for roll 110-Z that is greater than roll speed 520 determined for roll 110-Y. In one implementation, roll speeds 520/530 may be determined such that a tension value in yarn 170 (e.g., provided between rolls 110-Y and 110-Z) is a specific value (e.g., between ten to twenty grams) for providing optimum measurement of yarn 170 by camera 130. Rolls 110-X, 110-Y, and 110-Z may receive roll speeds 510-530, respectively, and may operate at roll speeds 510-530, respectively.

As further shown in FIG. 5, load cell 120-1 may measure tension 540 of yarn 170 provided between rolls 110-X and 110-Y, may set the roll speed(s) of rolls 110-X and/or 110-Y to a test-specific elongation level, and may fix the roll speed (s) of rolls 110-Y and/or 110-Z to an appropriate level for the first test run (e.g., to provide a 1% elongation level on yarn 170). In one implementation, load cell 120-1 may measure tension 540 of yarn 170 provided between rolls 110-X and 110-Y, and may provide tension 540 to computing device 150. Computing device 150 may receive tension 540, may determine if tension 540 is appropriate for the first test run (e.g., provides a 1% elongation level on yarn 170), and may adjust (if necessary) roll speeds 510 and/or 520 based on the determination. Load cell 120-2 may measure tension 550 of yarn 170 provided between rolls 110-Y and 110-Z, and may provide tension 550 to computing device 150. Computing device 150 may receive tension 550, may determine if tension 550 is appropriate for the first test run (e.g., at the specific value for optimum measurement of yarn 170), and may adjust (if necessary) roll speeds 520 and/or 530 based on the determination.

Camera 130 may provide yarn measurements 580, for the first test run, to computing device 150. Computing device 150 may also record a yarn elongation level (e.g., 1%) for the first test run (e.g., based on roll speeds 510/520 and/or tension 540), may record a number of entanglements in yarn 170 after the first test run (e.g., based on yarn measurements 580), and may calculate an entanglement strength value (e.g., 98% of entanglements remaining) of yarn 170 after the first test run.

Computing device 150 may increment the test run number by one (e.g., a second test run), and may determine whether the test run number (e.g. two) is greater than a particular number (e.g., twenty) of runs designated for the entanglement strength test. If the test run number is less than or equal to the designated number of test runs, the process described above in connection with the first test run may be repeated for subsequent test runs. However, each subsequent test run may apply (e.g., via adjustment of roll speeds 510/520 of rolls 110-X and 110-Y) a greater elongation level (e.g., yarn draw ratio) to yarn 170 so that more and more entanglements may be removed from yarn 170. If the test run number is greater than the designated number of test runs, computing device 150 may stop the entanglement strength test, may determine a final entanglement strength of yarn 170 (e.g., based on yarn measurements 580), and may provide a statistical summary for the test (e.g., based on yarn measurements 580).

In one implementation, computing device 150 may compare a number of entanglements in yarn 170 (e.g., determined during the first test run) to a number of entanglements initially in yarn 170 (e.g., determined during the initial test run) in order to calculate an entanglement strength value for yarn 170 (e.g., a number of entanglements remaining in yarn 170) after the first test run. Computing device 150 may also calculate a yarn elongation level for rolls 110-X and 110-Y (e.g., for the first test run) based on roll speeds 510/520 applied during the first test run. Computing device 150 may calculate an entanglement strength of yarn 170 (e.g., a percentage of entanglements remaining in yarn 170) based on the number of entanglements remaining in yarn 170 and the calculated elongation level. For example, if yarn 170 is to be used in a process that will stretch yarn 170 by 5% (e.g., an elongation level of 5%) and yarn 170 may only be able to be used in such a process if 10% or less of the entanglements remain in yarn, the calculated entanglement strength value for yarn 170 (e.g., a percentage of entanglements remaining in yarn 170) may be used to determine if yarn 170 is applicable to the process. Further details of information capable of being generated by computing device 150 are provided below in connection with FIG. 6.

Although FIG. 5 shows example operations capable of being performed by arrangement 100, in other implementations, arrangement 100 may perform fewer operations, different operations, or additional operations than depicted in FIG. 5. Alternatively, or additionally, one or more components of arrangement 100 may perform one or more other tasks described as being performed by one or more other components of arrangement 100.

Example Database Portion

FIG. 6 is a diagram of a portion of a database 600 capable of being provided in and/or managed by computing device 150. In one implementation, information in database portion 600 may be output by computing device 150 to an operator (e.g., of computing device 150). As illustrated, database portion 600 may include a variety of information associated with results of a yarn entanglement strength test. For example, database portion 600 may include a test data section that includes a test number field 605, a yarn elongation level (E %) field 610, a draw tension field 615, an entanglement strength (ES %) field 620, an average entanglement count (E-Count) field 625, an average skip length field 630, a maximum skip length field 635, a skip standard deviation (SD) field 640, a skip coefficient of variation (CV %) field 645, and/or a variety of entries 650 associated with fields 605-645.

Test number field 605 may include a test run number associated with test run of the yarn entanglement strength test. For example, a test run number of "0" may be associated with an initial test run, and a test run number of "1" may be associated with a first test run.

Yarn E % field 610 may include a yarn elongation level (e.g., provided via rolls 110-X and 110-Y) on yarn 170 for a particular test run number provided in test number field 605. For example, as shown in FIG. 6, yarn E % field 610 may indicate that a yarn elongation level of 5% is applied to yarn 170 during the sixth test run (e.g., provided in test number field 605).

Tension field 615 may include a tension (e.g., provided via rolls 110-X and 110-Y) on yarn 170 for a particular test run number provided in test number field 605. For example, as shown in FIG. 6, tension field 615 may indicate that a tension of 19.85 is applied to yarn 170 during the eighth test run (e.g., provided in test number field 605).

Entanglement strength (ES %) field 620 may include a percentage of entanglements remaining in yarn 170 after performance of the particular test run number provided in test number field 605. The percentages provided in ES % field 620 may be calculated by dividing the number of entanglements remaining in yarn 170 (e.g. after a particular test run) by the number of entanglements remaining in yarn 170 (e.g., after the initial test run). For example, as shown in FIG. 6, 90.2% of the entanglements may remain in yarn 170 after performance of the second test run (e.g., provided in test number field 605), 53.9% of the entanglements may remain in yarn 170 after performance of the third test run (e.g., provided in test number field 605), etc.

Entanglement count field 625 may include a number of entanglements (e.g., average entanglements per meter) remaining in yarn 170 after performance of the particular test run number provided in test number field 605. For example, as shown in FIG. 6, one-hundred (100) entanglements may remain in yarn 170 after performance of the initial test run (e.g., provided in test number field 605), 90.7 entanglements may remain in yarn 170 after performance of the first test run (e.g., provided in test number field 605), etc.

Average skip length field 630 may include an average length of skips in yarn 170 after performance of the particular test run number provided in test number field 605. For example, as shown in FIG. 6, skips in yarn 170 may have an average length of 1.10 (cm) after performance of the initial test run (e.g., provided in test number field 605).

Maximum skip length field 635 may include a maximum length of a skip in yarn 170 after performance of the particular test run number provided in test number field 605. For example, as shown in FIG. 6, a skip in yarn 170 may have a maximum length of 5.91 (cm) after performance of the initial test run (e.g., provided in test number field 605).

Skip SD field 640 may include a standard deviation associated with lengths of skips in yarn 170 after performance of the particular test run number provided in test number field 605. Skip CV % field 645 may include a coefficient of variation associated with lengths of skips in yarn 170 after performance of the particular test run number provided in test number field 605.

Returning to the example described above with respect to FIG. 5, yarn 170 may be used in a process that will stretch yarn 170 by 5% (e.g., an elongation level of 5%) and yarn 170 may only be able to be used in such a process if 10% or less of the entanglements remain in yarn 170 (e.g., an ES % value<10%). Computing device 150 may locate a yarn elongation level of 5% in E % field 610 and may locate the calculated percentage of entanglements remaining in yarn 170 (e.g., provided in ES % field 620) associated with the 5% yarn draw ratio. As shown in FIG. 6, less than 10% (e.g., 7.9%) of the entanglements may remain in yarn 170 at the 5% elongation level. Thus, yarn 170 may be applicable for the particular process. Thus, determining the entanglement strength of yarn 170 may enable a yarn producer to determine whether yarn 170 may be used to meet a particular process requirement, such as fabric production (e.g., that uses yarn 170 to make a fabric).

As further shown in FIG. 6, database portion 600 may include a summary data section 655 that provides a summary of information collected for different yarns. The summary for each series of test runs may contain the entanglement information for the initial test run (e.g., 0% elongation) and the last test run (e.g., the last elongation level). This may enable a quick view of the final entanglement strength for the yarn under test. For example, summary data section 655 may provide (e.g., for different yarns) information associated with a yarn identification (ID) field, a yarn package ID field, a yarn elongation level (E %) field, an entanglement strength (ES %) field, a tension field, an average entanglement count (E-Count) field, an average skip length field, a maximum skip length field, a skip standard deviation (SD) field, and a skip coefficient of variation (CV %) field. Such information may enable a comparison of properties associated with different yarns.

Although FIG. 6 shows example information that may be provided in database portion 600, in other implementations, database portion 600 may contain less information, different information, or additional information than depicted in FIG. 6. For example, although FIG. 6 shows twenty (20) test runs for the yarn entanglement strength test, in other implementations, the yarn entanglement strength test may include more or fewer than twenty (20) test runs.

Example Process

Figure 7B:
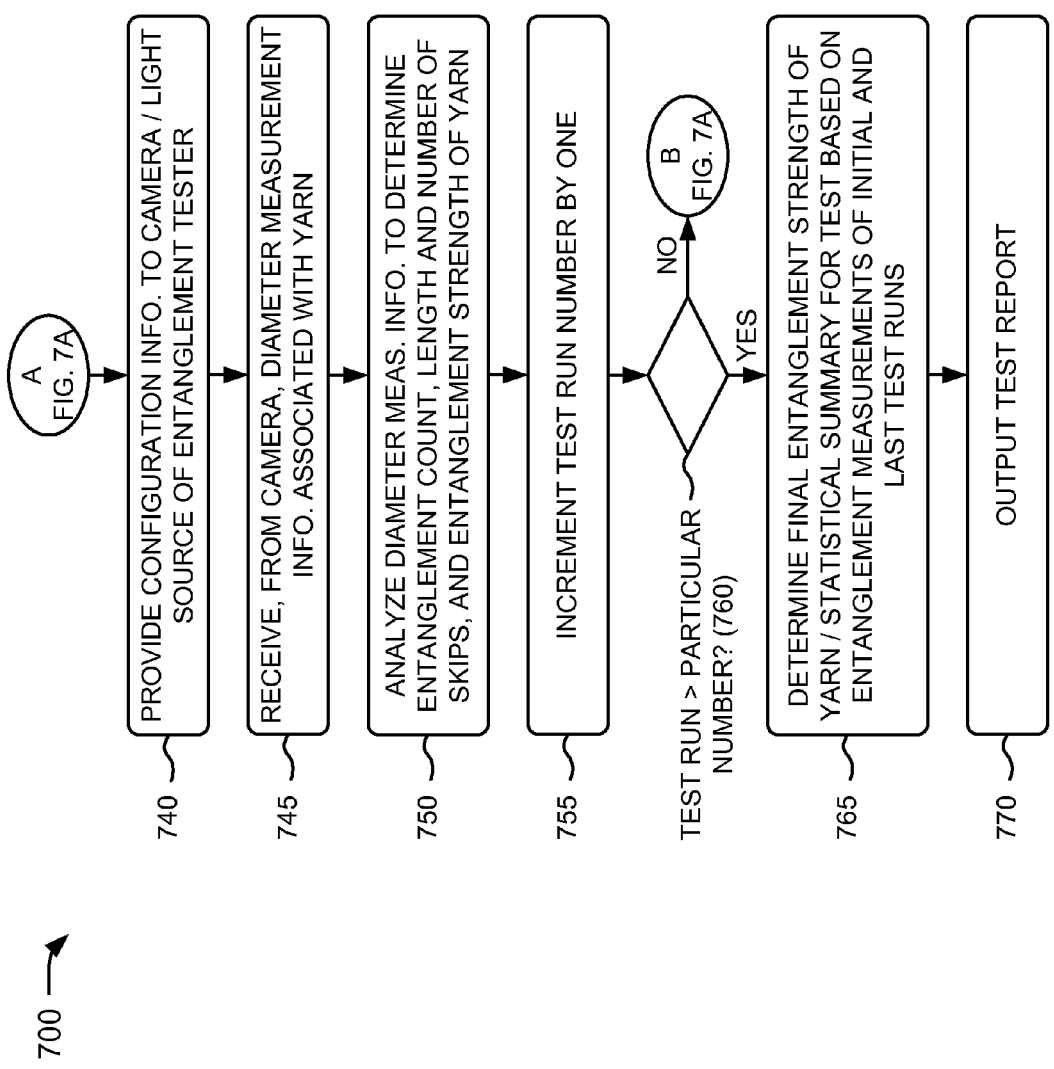
FIGS. 7A-8 are flow charts of an example process for determining an entanglement strength of yarn according to implementations described herein.
Figure 8:
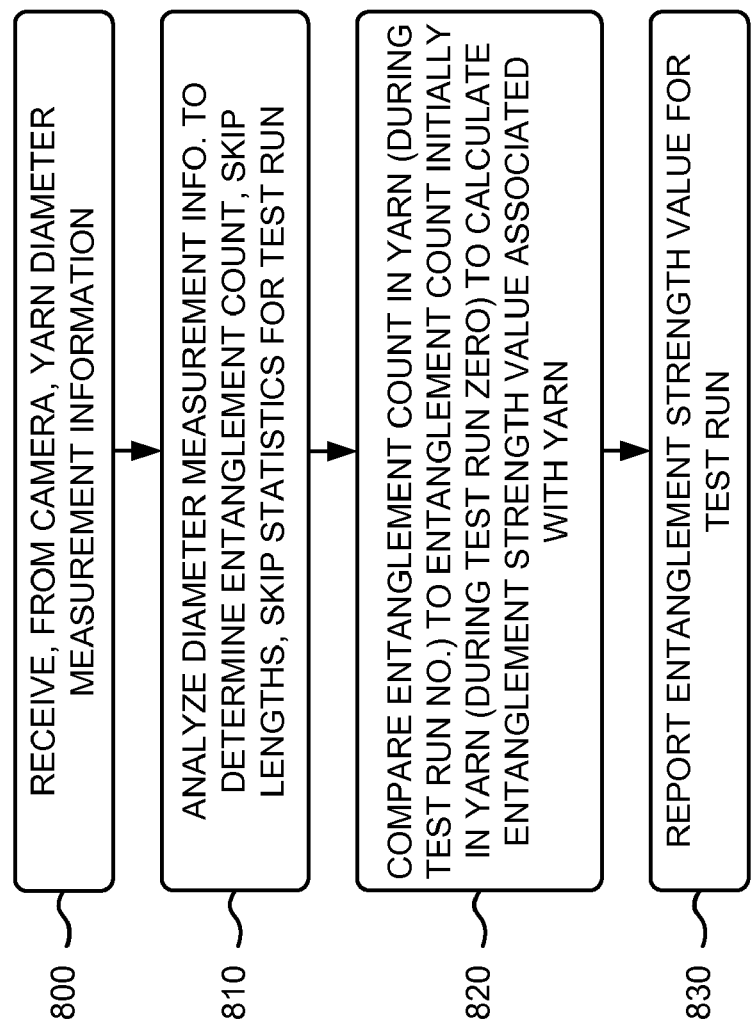

FIGS. 7A-8 are flow charts of an example process 700 for determining an entanglement strength of yarn according to implementations described herein. In one implementation, process 700 may be performed by computing device 150 (e.g., via motion control module 155). In another implementation, some or all of process 700 may be performed by another device or group of devices, including or excluding computing device 150.

As shown in FIG. 7A, process 700 may include setting a test run number to zero (block 705), determining a first roll speed for a first roll of an entanglement strength tester based on an elongation level specified for the test run (block 710), determining a second roll speed for a second roll of the entanglement strength tester based on a test speed specified for the test run (block 715), and determining a third roll speed for a third roll of the entanglement strength tester based on the determined second roll speed (block 720). For example, in implementations described above in connection with FIG. 5, computing device 150 may set a test run number to zero (e.g., an initial test number), and may determine roll speeds of rolls 110 based on a zero percent elongation level. In one example, the initial test run may not attempt to remove entanglements from yarn 170. Therefore, computing device 150 may determine roll speed 510 for roll 110-X that is the same speed as a roll speed 520 determined for roll 110-Y (e.g., so that yarn 170 may be driven from roll 110-X towards roll 110-Y but no entanglements may be removed from yarn 170). Computing device 150 may determine roll speed 530 for roll 110-Z that is greater than roll speed 520 determined for roll 110-Y. In one example, roll speeds 520/530 may be determined such that a tension value in yarn 170 (e.g., provided between rolls 110-Y and 110-Z) is a specific value (e.g., between ten to twenty grams) for providing optimum measurement of yarn 170 by camera 130.

As further shown in FIG. 7A, process 700 may include providing the determined roll speeds to the first, second, and third rolls (block 725), continuously receiving a tension measurement of yarn provided between the second and third rolls (block 730), and adjusting (if necessary) the third roll speed, based on the tension measurement, to provide an optimum tension for camera measurements of the yarn (block 735). For example, in implementations described above in connection with FIG. 5, computing device 150 may provide roll speed 510 to roll 110-X, may provide roll speed 520 to roll 110-Y, and may provide roll speed 530 to roll 110-Z. Rolls 110-X, 110-Y, and 110-Z may receive roll speeds 510-530, respectively, and may operate at roll speeds 510-530, respectively. Load cell 120-2 may measure tension 550 of yarn 170 provided between rolls 110-Y and 110-Z, and may provide tension 550 to computing device 150. Computing device 150 may receive tension 550, may determine if tension 550 is appropriate as an optimum tension for measurement by camera 130, and may adjust (if necessary) roll speeds 520 and/or 530 based on the determination.

As shown in FIG. 7B, process 700 may include providing configuration information to a camera and a light source of the entanglement strength tester (block 740), receiving, from the camera, diameter measurement information associated with the yarn (block 745), and analyzing the diameter measurement information to determine an entanglement count, a length and number of skips, and an entanglement strength of the yarn (block 750). For example, in implementations described above in connection with FIG. 5, computing device 150 may provide configuration information 560 to camera 130 and may provide configuration information 570 to light source 140. Configuration information 560 may include a scan rate of camera 130 and parameters such as exposure, pixel coefficients, camera gain, and other configuration parameters for camera 130. Configuration information 570 may include a light level to be provided by light source 140, a threshold for a desired light level to be provided by light source 140, etc. Camera 130 may provide yarn measurements 580 to computing device 150. Yarn measurements 580 may include diameters (e.g., a diameter profile) of yarn 170 that are captured by camera 130. Computing device 150 may record a yarn elongation level (e.g., 0%) for the initial test run (e.g., based on roll speeds 510/520 and/or tension 540), may calculate an initial number of entanglements in yarn 170 (e.g., based on yarn measurements 580), and may calculate a percentage of entanglements remaining (e.g., 100%) in yarn 170 after the initial test run.

Computing device 150 may set a threshold for determination of whether a diameter of yarn 170 constitutes an entanglement. If a diameter of yarn equals or is less than the entanglement threshold, computing device 150 may register the diameter as an entanglement (e.g., computing device 150 may increase an entanglement count by one). If a diameter of yarn 170 is greater than the entanglement threshold, computing device 150 may register the diameter as a skip. In one example, computing device 150 may measure the distance between threshold crossings to determine a length of a skip and/or a length of an entanglement. In another example, computing device 150 may filter out small unexpected crossings of the entanglement threshold that are too early for a valid new entanglement count.

Returning to FIG. 7B, process 700 may include incrementing the test run number by one (block 755), determining whether the incremented test run number is greater than a particular number (block 760). If the incremented test run number is not greater than the particular number (block 760—NO), process 700 may return to process block 710 (FIG. 7A). If the incremented test run number is greater than the particular number (block 760—YES), process 700 may include determining a final entanglement strength of the yarn and a statistical summary for the test based on the entanglement measurements of the initial and last test runs (block 765) and outputting a test report (block 770).

For example, in implementations described above in connection with FIG. 5, computing device 150 may increment the test run number by one (e.g., a second test run), and may determine whether the test run number (e.g. two) is greater than a particular number (e.g., twenty) of runs designated for the entanglement strength test. If the test run number is less than or equal to the designated number of test runs, the process described above in connection with the first test run may be repeated for subsequent test runs. However, each subsequent test run may apply (e.g., via adjustment of roll speeds 510/520 of rolls 110-X and 110-Y) a greater elongation level to yarn 170 so that more and more entanglements may be removed from yarn 170. If the test run number is greater than the designated number of test runs, computing device 150 may stop the entanglement strength test, may determine a final entanglement strength of yarn 170 (e.g., based on yarn measurements 580), and may provide a statistical summary for the test (e.g., based on yarn measurements 580).

Process blocks 745-770 may include the process blocks depicted in FIG. 8. As shown in FIG. 8, process blocks 745-770 may include receiving, from the camera, yarn diameter measurement information (block 800), and analyzing the yarn diameter measurement information to determine an entanglement count, skip lengths, and/or skip statistics for the test run (block 810). For example, in implementations described above in connection with FIG. 5, camera 130 may provide yarn measurements 580 (e.g., diameters or a diameter profile of yarn 170 that are captured by camera 130) to computing device 150. Computing device 150 may also record a yarn elongation level (e.g., 0%) for the initial test run (e.g., based on roll speeds 510/520 and/or tension 540), may calculate an initial number of entanglements in yarn 170 (e.g., based on yarn measurements 580), and may calculate a percentage of entanglements remaining (e.g., 100%) in yarn 170 after the initial test run. Computing device 150 may set a threshold for determination of whether a diameter of yarn 170 constitutes an entanglement. If a diameter of yarn equals or is less than the entanglement threshold, computing device 150 may register the diameter as an entanglement (e.g., computing device 150 may increase an entanglement count by one). If a diameter of yarn 170 is greater than the entanglement threshold, computing device 150 may register the diameter as a skip. In one example, computing device 150 may measure the distance between threshold crossings to determine a length of a skip and/or a length of an entanglement.

As further shown in FIG. 8, process blocks 745-770 may include comparing an entanglement count in the yarn (during a particular test run number) to an entanglement count initially in the yarn (e.g., during the initial test run) to calculate an entanglement strength value associated with the yarn (block 820) and reporting the entanglement strength value for the test run (block 830). For example, in implementations described above in connection with FIG. 5, computing device 150 may compare a number of entanglements in yarn 170 (e.g., determined during the first test run) to a number of entanglements initially in yarn 170 (e.g., determined during the initial test run) in order to calculate an entanglement strength value for yarn 170 (e.g., a number of entanglements remaining in yarn 170) after the first test run. Computing device 150 may also calculate a yarn elongation level for rolls 110-X and 110-Y (e.g., for the first test run) based on roll speeds 510/520 applied during the first test run. Computing device 150 may calculate an entanglement strength of yarn 170 (e.g., a percentage of entanglements remaining in yarn 170) based on the number of entanglements remaining in yarn 170 and the calculated elongation level. Computing device 150 may output the entanglement strength value for the first test run (e.g., as shown in database portion 600 of FIG. 6).

Systems and/or methods described herein may enable entanglement strengths of yarn to be automatically and continuously tested. Such systems and/or methods may enable expedient and accurate testing of yarn entanglement strengths by eliminating the inordinate time and inaccuracies associated with manual testing. If the yarn is determined (e.g., via the automatic testing) to have an inconsistent distribution profile of yarn entanglements and/or an undesirable level or length of skips, the yarn manufacturer may alter process parameters (e.g., via changes to the entanglement jets being used) to improve the distribution profile of yarn entanglements.

The foregoing description of implementations provides illustration and description, but is not intended to be exhaustive or to limit the invention to the precise form disclosed. Modifications and variations are possible in light of the above teachings or may be acquired from practice of the invention.

For example, while series of blocks have been described with regard to FIGS. 7A-8, the order of the blocks may be modified in other implementations. Further, non-dependent blocks may be performed in parallel.

It will be apparent that aspects, as described herein, may be implemented in many different forms of software, firmware, and hardware in the implementations illustrated in the figures. The actual software code or specialized control hardware used to implement embodiments described herein is not limiting of the invention. Thus, the operation and behavior of the embodiments were described without reference to the specific software code—it being understood that software and control hardware may be designed to implement the embodiments based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification.

No element, act, or instruction used in the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A computing device-implemented method for a yarn entanglement strength tester that includes a first roll, a second roll, a third roll, and a camera, the method comprising:

executing, by the computer device, a particular number of test runs on a yarn, the yarn including an initial quantity of entanglements, where executing each test run of the particular number of test runs includes:
        setting, by the computing device, a test run number to a first value,
        determining, by the computing device, a first roll speed for the first roll based on an elongation level specified for the test run number, determining, by the computing device, a second roll speed for the second roll based on the elongation level specified for the test run number, determining, by the computing device, a third roll speed for the third roll based on the second roll speed, causing, by the computing device, the first roll to operate at the first roll speed and the second roll to operate at the second roll speed to apply the elongation level specified for the test run number on a portion of the yarn provided between the first roll and the second roll, causing, by the computing device, the third roll to operate at the third roll speed to apply a constant elongation level on a portion of the yarn provided between the second roll and the third roll, receiving, by the computing device, a tension measurement of the portion of the yarn provided between the first roll and the second roll in response to causing the first roll to operate at the first roll speed and the second roll to operate at the second roll speed, calculating a draw ratio based on the tension measurement, receiving, by the computing device and from the camera, diameter measurement information associated with the portion of the yarn provided between the second roll and the third roll, analyzing, by the computing device, the diameter measurement information to determine entanglement measurement information associated with the yarn for the test run number, incrementing, by the computing device, the test run number to obtain an incremented test run number, based on analyzing the diameter measurement information, determining, by the computing device, whether the incremented test run number is greater than the particular number, and executing, by the computing device and when the incremented test run number is less than or equal to the particular number, another test run of the particular number of test runs; and determining, by the computing device and when the incremented test run number is greater than the particular number, a final entanglement strength of the yarn based on the entanglement measurement information and the calculated draw ratios.

2. The computing-device implemented method of claim 1, further comprising:
adjusting the first roll speed of the first roll, during one test run of the particular number of test runs, based on the the draw ratio calculated during the one test run of the particular number of test runs.

3. The computing device-implemented method of claim 1, where executing each of the particular number of test runs further includes:
receiving a tension measurement of the portion of the yarn provided between the second roll and the third roll;
calculating, based on the tension measurement of the portion of the yarn provided between the second roll and the third roll, a second draw ratio, where the second draw ratio is applied to the portion of the yarn provided between the second roll and the third roll; and
adjusting, based on the second draw ratio, the third roll speed to apply the constant elongation level on the portion of the yarn provided between the second roll and the third roll, where applying the constant elongation level to the portion of the yarn provided between the second roll and the third roll maintains a particular diameter measurement tension on a portion of the yarn captured by the camera.

4. The computing device-implemented method of claim 1, further comprising:
providing configuration information to the camera, and
where the third roll speed is determined further based on the configuration information.

5. The computing device-implemented method of claim 4, where the configuration information includes one or more of a scan rate of the camera, an exposure of the camera, pixel coefficients of the camera, or a gain associated with the camera.

6. The computing device-implemented method of claim 1, where determining the final entanglement strength of the yarn comprises:
analyzing the diameter measurement information to determine an entanglement count in the yarn during each test run of the particular number of test runs; and
comparing the entanglement count in the yarn, during each test run of the particular number of test runs, to an initial entanglement count of the yarn, to calculate an entanglement strength value of the yarn after each test run of the particular number of test runs.

7. The computing device-implemented method of claim 1, where the first roll speed equals the second roll speed, when the test run number equals the first value to apply a zero percent elongation to the yarn provided between the first roll and the second roll during a first test run of the particular number of test runs.

8. The computing device-implemented method of claim 1, where, for each test run of the particular number of test runs, causing the second roll to operate at the second roll speed and causing the third roll to operate at the third roll speed maintains a particular diameter measurement tension on a portion of the yarn captured by the camera.

9. The computing device-implemented method of claim 1, where the yarn includes an initial quantity of entanglements, where analyzing the diameter measurement information includes:
determining, based on the diameter measurement information, a quantity of entanglements in the yarn after applying the elongation level specified for the test run number, and
determining, based on the initial quantity of entanglements and the quantity of entanglements in the yarn after applying the elongation level specified for the test run number, a quantity of entanglements removed from the yarn during each of the particular number of test runs, and
where determining the final entanglement strength of the yarn is further based on the determined quantity of entanglements removed from the yarn during each test run of the particular number of test runs.

10. A computing device-implemented method for a yarn entanglement strength tester that includes a first roll, a second roll, a third roll, and a camera, the method comprising:
determining, by the computing device, that the first roll and the second roll do not provide an elongation level on a portion of a yarn provided between the first roll and the second roll;
receiving, by the computing device and from the camera, initial images of diameters of a portion of the yarn provided between the second roll and the third roll in response to determining that the first roll and the second roll do not provide the elongation level on the yarn;

determining, by the computing device, an initial entanglement count in the yarn based on the initial images of the diameters of the yarn;

causing, by the computing device, the first roll and the second roll to apply incrementally increasing elongation levels on the portion of the yarn provided between the first roll and the second roll, where causing the first roll and the second roll to apply the incrementally increasing elongation levels includes:

receiving a tension measurement associated with the portion of the yarn provided between the first roll and the second roll as each of the incrementally increasing elongation levels are applied to the portion of the yarn provided between the first roll and the second roll, calculating, based on the tension measurement, a draw ratio of the portion of the yarn provided between the first roll and the second roll as each of the incrementally increasing elongation levels are applied to the portion of the yarn provided between the first roll and the second roll, and adjusting a roll speed of the first roll relative to a roll speed of the second roll based on the calculated draw ratio;

receiving, by the computing device and from the camera, images of diameters of the portion of the yarn provided between the second roll and the third roll after each of the incrementally increasing elongation levels are applied to the portion of the yarn provided between the first roll and the second roll;

determining, by the computing device, an entanglement count in the yarn based on the images of the diameters of the portion of the yarn provided between the second roll and the third roll after each of the incrementally increasing elongation levels are applied to the portion of the yarn provided between the first roll and the second roll;

comparing, by the computing device, the determined entanglement count in the yarn to the initial entanglement count in the yarn to determine a quantity of entanglements remaining in the yarn after each of the incrementally increasing elongation levels is applied to the portion of the yarn provided between the first roll and the second roll; and determining, by the computing device, an entanglement strength value of the yarn based on the calculated draw ratios and the quantity of entanglements remaining in the yarn after each of the increasing elongation levels are applied to the portion of the yarn provided between the first roll and the second roll.

11. The computing device-implemented method of claim 10, where adjusting the roll speed of the first roll relative to the roll speed of the second roll comprises:

determining a plurality of first roll speeds for the first roll;

determining a plurality of second roll speeds for the second roll, where each of the plurality of second roll speeds is greater than and associated with a corresponding one of the plurality of first roll speeds;

causing the first roll to operate at one of the plurality of the first roll speeds based on each of the calculated draw ratios; and causing the second roll to operate at one of the plurality of the second roll speeds based on causing the first roll to operate at the one of the plurality of first roll speeds, where operating the first roll at one of the plurality of the first roll speeds and operating the second roll at one of the plurality of the second roll speeds applies one of the incrementally increasing elongation levels on the yarn.

12. The computing device-implemented method of claim 10, further comprising:

instructing a light source, facing the camera, to provide light to a portion of the yarn not facing the camera.

13. The computing device-implemented method of claim 10, further comprising:

causing the second roll and the third roll to apply a particular diameter measurement tension on the portion of the yarn provided between the second roll and the third roll based on a scan rate of the camera.

14. The computing device-implemented method of claim 10, where a first roll speed of the first roll equals a second roll speed of the second roll, when the first roll and the second roll are determined not to provide the elongation on the portion of the yarn provided between the first roll and the second roll.

15. The computing-device implemented method of claim 10, where determining that the first roll and the second roll do not provide the elongation level on the portion of the yarn provided between the first roll and the second roll includes:

receiving, from a load cell of the yarn entanglement tester, a measurement of a tension on the portion of the yarn provided between the first roll and the second roll, determining, based on the measurement of the tension, whether the first roll and the second roll provide the elongation level on the portion of the yarn provided between the first roll and the second roll, and adjusting, when the first roll and the second roll provide the elongation level on the portion of the yarn provided between the first roll and the second roll, a speed of the first roll relative to a speed of the second roll to cause the first roll and the second roll to not provide the elongation level on the portion of the yarn provided between the first roll and the second roll.

16. A computing device, comprising:

a memory to store a plurality of instructions; and a processor to execute instructions in the memory to:

determine that a first roll and a second roll, of a yarn entanglement strength tester, provide a zero percent elongation level on a first portion of a yarn, receive, from a camera of the yarn entanglement strength tester, initial images of diameters of the yarn based on determining that the first roll and the second roll provide the zero percent elongation level on the yarn, determine an initial entanglement count in the yarn based on the initial images of the diameters of the yarn, cause the first roll and the second roll to apply incrementally increasing elongation levels on the first portion of the yarn, where, when causing the first roll and the second roll to apply the incrementally increasing elongation levels, the processor executes instructions in the memory to:

determine a tension associated with the first portion of the yarn as each of the incrementally increasing elongation levels are applied to the first portion of the yarn, and calculate, based on the determined tension, a draw ratio of the first portion of the yarn as each of the incrementally increasing elongation levels are applied to the first portion of the yarn, receive, from the camera, images of diameters of the yarn after each of the incrementally increasing elongation levels are applied to the first portion of the yarn, determine entanglement counts associated with the yarn based on the images of diameters of the yarn after each of the incrementally increasing elongation levels is applied to the first portion of the yarn, compare the determined entanglement counts in the yarn to the initial entanglement count in the yarn to calculate a quantity of entanglements remaining in the yarn after each of the incrementally increasing elongation levels are applied to the first portion of the yarn, and calculate a strength value associated with the yarn based on the draw ratios and the quantities of entanglements remaining in the yarn.

17. The computing device of claim 16, where, when causing the first roll and the second roll to apply incrementally increasing elongation levels on the first portion of the yarn, the processor is further to execute instructions in the memory to:

determine a plurality of first roll speeds for the first roll, determine a plurality of second roll speeds for the second roll, where each of the plurality of second roll speeds is greater than and associated with a corresponding one of the plurality of first roll speeds, cause, based on the calculated draw ratios, the first roll to operate at one of the plurality of the first roll speeds, and cause, based on causing the first roll to operate at the one of the plurality of the first roll speeds, the second roll to operate at the corresponding one of the plurality of the second roll speeds, where the first roll operating at the one of the plurality of the first roll speeds and the second roll operating at the one of the plurality of the second roll speeds applies the incrementally increasing elongation levels on the yarn.

18. The computing device of claim 16, where the processor is further to execute instructions in the memory to:

instruct a light source, facing the camera, to provide light to a portion of the yarn not facing the camera.

19. The computing device of claim 16, where the yarn entanglement strength tester includes a third roll, and the processor is further to execute instructions in the memory to:

cause the second roll and the third roll to apply a particular diameter measurement tension on a second portion of the yarn provided between the second roll and the third roll.

20. The computing device of claim 16, where a roll speed of the first roll equals a roll speed of the second roll, when the first roll and the second roll provide the zero percent elongation on the first portion of the yarn.

21. A yarn entanglement strength tester, comprising:

a first roll to receive a yarn that includes a plurality of entanglements;

a second roll to receive the yarn from the first roll, where the first roll and the second roll apply incrementally increasing elongation levels on the yarn to remove one or more of the plurality of entanglements from the yarn;

a first load cell provided between the first roll and the second roll, where the first load cell determines a measurement associated with a first portion of the yarn provided between the first roll and the second roll as the incrementally increasing elongation levels are applied on the yarn;

a third roll to receive the yarn from the second roll, where the second roll and the third roll apply a particular diameter measurement tension on a second portion of the yarn provided between the second roll and the third roll as the incrementally increasing elongation levels are applied on the yarn;

a second load cell provided between the second roll and the third roll, where the second load cell determines a measurement associated with the particular diameter measurement tension applied on the second portion of the yarn;

a camera provided between the second roll and the third roll, where the camera captures images of diameters of the yarn after each of the incrementally increasing elongation levels are applied to the yarn;

a light source provided between the second roll and the third roll and facing the camera, where the light source provides light to a portion of the yarn; and a computing device to:

control operation of the first roll, the second roll, the third roll, the first load cell, the second load cell, the camera, and the light source, determine, based on the captured images, a quantity of the plurality of entanglements removed from the yarn after each of the incrementally increasing elongation levels are applied to the yarn, calculate, based on the measurement associated with the first portion of the yarn and the measurement associated with the particular diameter measurement tension applied to the second portion of the yarn, draw ratios associated with each of the incrementally increasing elongation levels, and determine an entanglement strength value for the yarn based on the captured images of the diameters of the yarn, the quantity of the plurality of entanglements removed from the yarn, and the calculated draw ratios.

22. The yarn entanglement strength tester of claim 21, where the computing device further:

determines that a zero percent elongation is applied on the first portion of the yarn, receives, from the camera, initial images of diameters of the yarn based on the zero percent elongation being applied on the first portion of the yarn, and determines an initial entanglement count associated with the plurality of entanglements in the yarn based on the initial images of the diameters of the yarn, where, when controlling the operation of the first roll, the second roll, the third roll, the first load cell, the second load cell, the camera, and the light source, the computing device:

instructs the first roll and the second roll to apply the incrementally increasing elongation levels on the first portion of the yarn, receives, from the camera, images of diameters of the yarn associated with applying each of the incrementally increasing elongation levels to the yarn, and determines entanglement counts in the yarn based on the images of diameters of the yarn after each of the incrementally increasing elongation levels is applied to the yarn, where the computing device further determines the quantity of the plurality of entanglements removed from the yarn after each of the incrementally increasing elongation levels are applied to the yarn further based on the determined entanglement counts in the yarn.

23. The yarn entanglement strength tester of claim 21, where, when controlling the operation of the first roll, the second roll, the third roll, the first load cell, the second load cell, the camera, and the light source, the computing device:

determines a plurality of first roll speeds for the first roll, determines a plurality of second roll speeds for the second roll, where each of the plurality of second roll speeds is greater than and associated with a corresponding one of the plurality of first roll speeds, causes the first roll to operate at the plurality of the first roll speeds, and causes the second roll to operate at the plurality of the second roll speeds, where the first roll operating at the plurality of the first roll speeds and the second roll operating at the plurality of the second roll speeds applies the incrementally increasing elongation levels on the yarn.

24. The yarn entanglement strength tester of claim 21, where, when controlling the operation of the first roll, the second roll, the third roll, the first load cell, the second load cell, the camera, and the light source, the computing device is further to:

receive a measurement of one of the incrementally increasing elongation levels from the first load cell, calculate, based on the received measurement, a draw ratio associated with the one of the incrementally increasing elongation levels, and adjust, based on the draw ratio associated with the one of the incrementally increasing elongation levels, a speed of the first roll relative to a speed of the second roll to modify the one of the incrementally increasing elongation levels applied on the first portion of the yarn.

\* \* \* \* \*